United States Patent [19]

Habermann

[11] 4,329,500

[45] May 11, 1982

[54] CATALYSTS FOR THE HYDRATION OF NITRILES TO AMIDES

[75] Inventor: Clarence E. Habermann, Midland, Mich.

[73] Assignee: The Dow Chemical Company, Midland, Mich.

[21] Appl. No.: 931,571

[22] Filed: Aug. 7, 1978

Related U.S. Application Data

[60] Continuation of Ser. No. 442,271, Feb. 13, 1974, abandoned, which is a division of Ser. No. 91,146, Nov. 19, 1970, abandoned.

[51] Int. Cl.$^3$ ............................................. C07C 102/08
[52] U.S. Cl. ..................................... 564/128; 564/126
[58] Field of Search ........... 260/558 R, 561 R, 561 N; 252/470; 564/126, 128

[56] References Cited

U.S. PATENT DOCUMENTS

| | | | |
|---|---|---|---|
| 3,499,879 | 3/1970 | Kobayashi et al. | 260/561 N X |
| 3,597,481 | 8/1971 | Tefertiller et al. | 260/561 N |
| 3,631,104 | 12/1971 | Habermann et al. | 260/561 RX |
| 3,670,021 | 6/1972 | Goetz et al. | 260/561 N X |
| 3,696,152 | 10/1972 | Habermann et al. | 260/561 R X |
| 3,751,465 | 8/1973 | Takehashi et al. | 260/561 R |
| 3,758,576 | 9/1973 | Takehashi et al. | 260/561 R |
| 3,794,682 | 2/1974 | Barber | 260/561 N |
| 3,997,606 | 12/1976 | Kane | 260/561 N |
| 4,036,879 | 7/1977 | Habermann | 260/561 N |
| 4,056,565 | 11/1977 | Matsuda | 260/561 N |

OTHER PUBLICATIONS

Kobayashi et al., CA 70:114859n (1969).
Murakami et al., CA 60:4053c (1964).

*Primary Examiner*—Thomas A. Waltz
*Attorney, Agent, or Firm*—Charles J. Enright

[57] ABSTRACT

A process for hydrating a nitrile to the corresponding amide by contacting the nitrile in the presence of water with an essentially insoluble heterogeneous catalyst selected from the group consisting of unreduced and reduced cobalt oxide and unreduced and reduced cobalt-chromium oxide or mixture thereof.

2 Claims, No Drawings

CATALYSTS FOR THE HYDRATION OF NITRILES TO AMIDES

CROSS-REFERENCE TO RELATED APPLICATIONS

This is a continuation of my copending application Ser. No. 442,271 filed Feb. 13, 1974, which in turn is a division of application Ser. No. 91,146 filed Nov. 19, 1970, both now abandoned.

BACKGROUND OF THE INVENTION

The conversion of a nitrile to the corresponding amide is carried out on a commercial scale by sulfuric acid hydration. This process requires extensive amounts of expensive equipment, and in addition provides an undesirable source of sulfate pollution. Other methods of converting a nitrile to the amide are also known, see for example, Mahon in U.S. Pat. Nos. 2,421,030, Haefele in 3,366,639 and Watanabe in Bull. Chem. Soc. Japan, 32, 1280 (1959), 37, 1325 (1964) and 39, 8 (1966). The basic problem encountered has been the development of a suitable catalyst which would be feasible for the successful application of these operations to commercial production.

SUMMARY OF THE INVENTION

It has now been found according to the present invention that nitriles can be converted to the corresponding amide by contacting the nitrile in the presence of water with an essentially insoluble heterogeneous catalyst selected from the group consisting of unreduced and reduced cobalt oxide and unreduced and reduced cobalt-chromium oxide or mixture thereof. By the use of these catalysts, good conversions and yields are obtained in a convenient reaction without deleteriously affecting the environment.

The important and novel aspect of the present invention is the use of the specific catalysts named above in the conversion of a nitrile to the corresponding amide by contacting the nitrile in water with the catalyst.

Generically, the catalysts are prepared by forming the oxide or a mixture of oxides and then reducing the oxide when required with a suitable reducing agent. Various techniques for both of these steps in the catalyst preparation are known.

The proportions of the component metals in those catalysts containing two or more metals are not critical and may vary widely so long as any significant proportion of each is present.

The oxide or oxide mixture is suitably prepared by precipitation of the soluble components of the catalyst, preferably as the carbonate salt and decomposing the carbonate to the corresponding oxide. For example, cobalt oxide may be purchased commercially or prepared by adding a solution of ammonium carbonate to a solution of cobalt nitrate to form a precipitate of cobalt carbonate. This precipitate is then decomposed by heat to give the desired cobalt oxide. In a manner similar to those preparations described by Butts (Copper, Reinhold, New York (1954) beginning at page 842) and Adkins (Reactions of Hydrogen, U. of Wis. Press, Madison, Wis. (1937) beginning at page 12) for copper-chromium oxide catalysts, the catalysts of the invention may be prepared. By any of these preparations, the final product is the oxide or mixture of oxides. In those cases where the unreduced catalyst is employed, the catalyst is used without further treatment.

The reduced catalysts are prepared by treating the mixture of oxides with an additional step. This second step involves contacting the oxide or oxide mixture with a suitable reducing agent until a desirable catalyst is obtained. Although numerous reducing agents may be utilized in the reduction, the use of hydrogen as the reducing agent is preferred since the adverse effect on the catalyst is minimized because of the volatile by-products.

The active catalysts of the invention may be used alone or mounted on a support. Representative examples of suitable supports include alumina, silica, silica gel, charcoal, magnesia, chromia, iron oxide and clays. Of course, the weight of active catalyst in supported catalysts compared to the total weight of the catalyst is proportionally smaller than those values described above for unsupported catalysts.

The catalysts of the present invention are used to convert a nitrile to the corresponding amide in either a batch or a continuous process. In either process, the nitrile and water are contacted with the catalyst under the appropriate reaction conditions and the amide product is then recovered. Since the catalysts of the present invention are essentially insoluble, heterogeneous catalysts, a continuous flow reaction is preferred.

In a continuous flow reaction, the solid catalyst of the invention is placed into a reaction chamber having an inlet for reactants and an outlet for products. The reaction chamber is maintained at the desired reaction temperature and the rate of flow of the reactants over the catalysts is controlled to give the desired contact of the reactants with the catalyst. The reactants may be fed over the solid catalyst as a gas or preferably as a liquid. The reaction product from the reactor may suitably be used as such or purified by any conventional technique.

The process of the present invention is suitably applicable to any nitrile, with aliphatic and aromatic hydrocarbon nitriles containing up to about 20 or more carbon atoms being preferred. For purpose of the invention, aromatic nitriles are defined as those nitriles having cyano groups attached to the aromatic nucleus. Representative examples of suitable nitriles include: saturated aliphatic hydrocarbon nitriles such as acetonitrile, propionitrile, pentanonitrile, dodecanonitrile, succinonitrile, adiponitrile and the like; unsaturated aliphatic hydrocarbon nitriles such as acrylonitrile, methacrylonitrile, crotonic nitrile, $\beta$-phenylacrylonitrile, 2-cyano-2-butene, 1-cyano-1-octene, 10-undecenonitrile, maleonitrile, fumaronitrile and the like; and aromatic nitriles such as benzonitrile, p-toluonitrile, $\alpha$-naphthonitrile, phthalonitrile and the like. Of the nitriles suitable for use in the invention, the olefinic nitriles of 3 to about 6 carbon atoms are especially preferred, with the conversion of acrylonitrile to acrylamide being of special interest.

The proportions of nitrile to water in the reactant mixture may vary widely. More important than the specific nitrile to water ratio is the extent of the interaction between the nitrile and water. A high degree of contact is desirable to assure the greatest efficiency in the reaction. For gaseous reactants, the nitrile and water are miscible in all proportions, but for liquid reactants, certain precautions may be necessary to insure that sufficient contact of the nitrile and water is maintained. The necessary contact may be realized by dissolving the nitrile in the water or by dissolving the water in the nitrile. Outside of the limits of the solubility of one of the reactants in the other, however, the reactant mixture may be agitated, a suitable solvent may be added or another means of increasing the contact of the reactants may be employed. Excess water is the preferred solvent although other inert solvents, such as dioxane, dimethyl sulfoxide, acetone, dimethyl ether of ethylene glycol or tetrahydrofuran, may also be used.

The temperature of the reaction may vary widely as different nitriles and catalysts are used in the invention. Generally, the reaction is conducted within a temperature range of about 0° to about 400° C. At temperatures below this range, the reaction is impractically slow. Above this range, the reaction forms an increasing amount of undesirable by-products. Within the broad temperature range, temperatures of about 25° to about 200° C. or more are preferred. For unsaturated nitriles which tend to polymerize, the use of a reaction temperature of less than about 200° C. or the use of dilute solutions is desirable to avoid polymerization of the nitrile and possible poisoning of the catalyst.

The other reaction conditions and techniques for the use of heterogeneous catalysts are known and not critical to the invention. The important aspect of the invention is using a catalyst defined above to convert a nitrile to the corresponding amide.

EXAMPLE 1

Unreduced Cobalt Oxide

In a liter of water, 48 g. of $(NH_4)_2CO_3$ was dissolved, and in a second liter of water 145.5 g. of $Co(NO_3)_2 \cdot 6H_2O$ was dissolved. The carbonate solution was slowly added to the cobalt solution. The mixture was stirred during the addition and for 10 minutes thereafter. The precipitate was allowed to settle and the solution was decanted. The remaining solid was washed several times with water, separated by filtration, dried at 85° C. in an air oven and then decomposed at 225° C. for 5 hours to give cobalt oxide. One gram of the catalyst was added to a glass ampoule with 5 g. of a 7% solution of acrylonitrile in water. The ampoule was sealed, heated at 80° C. for 1 hour and quickly cooled. The contents were analyzed by gas-liquid chromatography for the remaining acrylonitrile and the presence of acrylamide. The result of this is shown in Table I.

TABLE I

Conversion of Acrylonitrile to Acrylamide using Various Catalysts

| Example | Catalyst | Conversion of Acrylonitrile, % | Yield of Acrylamide, % |
|---|---|---|---|
| 1 | Unreduced Cobalt Oxide | 43 | 69 |

In the same manner as shown by the example above, the catalyst is used to hydrate other nitriles, such as acetonitrile, benzonitrile, adiponitrile and methacrylonitrile, to the corresponding amide. Also in a similar manner to that shown above, the catalyst of the example is combined with reduced copper-metal oxides, such as reduced copper-aluminum oxide, reduced copper-chromium oxide, reduced copper-cobalt oxide, reduced copper-zinc oxide or reduced copper-yttrium oxide, copper-silicon oxide and the mixtures are used to hydrate nitriles of up to 20 carbon atoms to the corresponding amide.

I claim:

1. In the process of hydrating a nitrile to the corresponding amide by contacting the nitrile in the presence of water with a catalyst, the improvement comprising using as catalyst unreduced cobalt oxide.

2. The process of claim 1 wherein the nitrile is acrylonitrile.

* * * * *